(12) United States Patent
Sarangapani et al.

(10) Patent No.: US 8,632,545 B2
(45) Date of Patent: Jan. 21, 2014

(54) BONE PLATES AND BONE PLATE ASSEMBLIES

(75) Inventors: Ravi Sarangapani, Pune (IN);
Shirkrishna Sadanand Joshi, Devrukh (IN); Ajit Arvind Phadke, Thane (IN)

(73) Assignee: Adler Mediequip Private Limited, Pune (IN)

( * ) Notice: Subject to any disclaimer, the term of this patent is extended or adjusted under 35 U.S.C. 154(b) by 335 days.

(21) Appl. No.: 12/675,692

(22) PCT Filed: Aug. 27, 2008

(86) PCT No.: PCT/IN2008/000541
§ 371 (c)(1),
(2), (4) Date: Feb. 26, 2010

(87) PCT Pub. No.: WO2009/063489
PCT Pub. Date: May 22, 2009

(65) Prior Publication Data
US 2010/0305570 A1    Dec. 2, 2010

(30) Foreign Application Priority Data
Aug. 27, 2007   (IN) .......................... 1641/MUM/2007

(51) Int. Cl.
| A61B 17/56 | (2006.01) |
| A61B 17/58 | (2006.01) |
| A61B 17/80 | (2006.01) |
| A61F 2/30  | (2006.01) |

(52) U.S. Cl.
USPC ................................ 606/71; 606/70; 606/280

(58) Field of Classification Search
USPC .................. 606/280–299, 70, 71, 96
See application file for complete search history.

(56) References Cited

U.S. PATENT DOCUMENTS

| RE28,841 | E  | * | 6/1976  | Allgower et al. ............. 606/282 |
| 5,147,361 | A  | * | 9/1992  | Ojima et al. ..................... 606/70 |
| 5,709,686 | A  | * | 1/1998  | Talos et al. ..................... 606/281 |
| 5,755,721 | A  | * | 5/1998  | Hearn .............................. 606/96 |
| 6,656,184 | B1 | * | 12/2003 | White et al. ................... 606/318 |
| 6,669,701 | B2 |   | 12/2003 | Steiner et al. |
| 6,719,759 | B2 | * | 4/2004  | Wagner et al. ................. 606/282 |
| 6,730,091 | B1 | * | 5/2004  | Pfefferle et al. ................ 606/70 |
| 2005/0070904 | A1 | * | 3/2005 | Gerlach et al. ................. 606/69 |
| 2005/0131413 | A1 |   | 6/2005 | O'Driscoll et al. |
| 2006/0264946 | A1 | * | 11/2006 | Young ............................. 606/69 |
| 2007/0055249 | A1 | * | 3/2007 | Jensen et al. .................... 606/69 |
| 2007/0162020 | A1 |   | 7/2007 | Gerlach et al. |
| 2007/0276386 | A1 | * | 11/2007 | Gerlach et al. ................. 606/72 |

FOREIGN PATENT DOCUMENTS

WO         2007079814 A1    7/2007

* cited by examiner

*Primary Examiner* — Kevin T Truong
*Assistant Examiner* — Si Ming Lee
(74) *Attorney, Agent, or Firm* — Kramer Amado, P.C.

(57) ABSTRACT

The invention relates to bone plate assembly having bone plate and bone screws for compressing and locking of bone plates for stabilizing fractured fragments of a bone.

20 Claims, 6 Drawing Sheets

BONE PLATES AND BONE PLATE ASSEMBLIES

TECHNICAL FIELD OF THE INVENTION

The instant invention relates to devices for fixation of fragments of a fractured bone. More particularly the invention relates to, bone plates and bone plate assemblies or bone plate systems for compression and stabilisation of fragments of a fractured bone.

BACKGROUND AND PRIOR ART

Fractures of bone generally involve complex injuries to surrounding soft tissues as well, which when treated conservatively often leads to misalignment, delayed or non-union of the fracture and stiffness of adjacent joints. It is well understood that fractures of bone that are treated with anatomical reduction and stable internal fixation using bone plates and bone screws are highly successful. Anatomical reduction and stable internal fixation are typically achieved using 'compression' screws wherein the hole in the bone plate is configured to enable the bone screw to glide within the hole and translate the bone fragment against the opposing bone fragment to enable compression of the two bone fragments against each other. Such a nature of fixation is typically understood to provide good clinical outcomes in fractures of the shaft or diaphyseal region of bone or for the fixation of joint fractures.

It is also well understood that bone healing can also result from relative stability or so-called flexible osteosynthesis whereby good clinical outcomes are obtained through maintenance of correct length, axis and rotation of the fractured bone fragments, rather than precise anatomical reduction and absolute stability or so called rigid fixation. Such a method of bone fixation is typically embodied in comminuted fractures where the goal is to maintain length of the bone and keep the end portions of the bone or the joints in correct position without directly fixing or manipulating the fracture zone itself. Existing solutions to enable this goal exist in the form of plate and screw systems where the bone screws are locked in the holes of the bone plate. The locked bone screws and bone plate form a stable construct and the stiffness of this construct provides stability to the fractured segments of bone. Locking of the bone screws in the plate hole ensures angular as well as axial stability, eliminates the possibility of toggling of the screw in the plate hole and thereby greatly reduces the risk of loss of reduction of the fractured fragments of bone, postoperatively. It is well known to a person skilled in the art that while these locking screws provide excellent angular stability and resistance to torsional and shear forces, they do not have the capability of compressing bone fragments.

As the regions of bone where fractures occur as well as the nature of fractures vary greatly, many fractures are not easily amenable to only rigid osteosynthesis with compression fixation alone or flexible osteosynthesis with angular stability alone. These situations led to an increasing need felt for bone plate assemblies which would allow either compression fixation or angle stable fixation with the nature of fixation of individual bone screws in individual plate holes being an intraoperative decision made by the operative surgeon depending on the nature of the fracture and the type of fixation required.

Bone plate assemblies that combine screws that enable compression of fracture fragments and screws that lock into the plate hole in a position of angular stability, typically having threads on the screw head, have been the subject of several patents and publications and are well known to those skilled in the art.

U.S. Pat. No. 6,669,701 discloses a bone plate with at least one hole including a first portion defining a substantially circular outer periphery and a second portion defining an elongated outer periphery and, with a plurality of threads disposed on the first portion, wherein the threads extend over an angle of 200 to 270 degrees at the upper surface of the bone plate and 180 to 230 degrees at the lower surface of the bone plate, with the first portion of the hole having threads configured to engage the threads on the head of a bone screw and the second portion of the hole configured to cooperate with the head of a different bone screw to provide compression to the fracture.

The bone plate as disclosed in the '701 patent has only a partial thread in the hole of the bone plate which does not circumscribe the diameter of the plate hole completely. Hence, screws used through such bone plates may not be able to absolutely maintain the desired fixed angular relationship between the bone plates and the bone screws under physiologic loads. Specifically, the screws within the plate are only partially captured and thus only partially surrounded by threads. Under high stress and loading conditions, the partially threaded hole in the bone plate may distort and allow the fixed angular relationship between the screw and the bone plate to change, resulting in a loss of fixation or loss of established intraoperative plate orientation.

US application 2007/0162020 remedies this disadvantage of a partial thread by disclosing a bone plate with a hole including a frustoconical portion and a thread that makes a complete revolution around the hole, a fastener with a spherical head to engage the frustoconical portion of the hole with a bone engaging portion, such that fine adjustment of a fracture is possible and a second fastener with a threaded head to engage the thread of the hole.

Such types of bone plate assemblies typically enable the use of either, one type of bone screw, typically with a spherical head that cooperates with a corresponding portion of the hole in the bone plate, to enable fracture fragment compression (compression screws) and rigid osteosynthesis, or, alternately, a second type of screw, typically with threads in the head that threadably engage with corresponding threads in a hole of the bone plate (locking screw), to enable an angular stability between the locking screw and the bone plate.

It is well understood that bone screws used in bone plate assemblies to compress bone fragments to one another, also compress the bone plate itself to the surface of the bone to obtain stability of the assembly. It is further well known that the resulting compression of the undersurface of the plate onto the surface of the bone leads to a compromise of the blood supply to the bone leading to stress shielding of the bone and resultant increase in the risk of poor clinical outcomes.

Further, fractures in osteoporotic bones form a significant proportion of all types of fractures that occur. One of the important characteristics of osteoporotic bones is that the poor bone quality does not allow good holding of the bone screws in the bone itself. U.S. Pat. No. '701 describes the use of bone plates with threads configured to engage the threads on the head of a bone screw to provide angular and axial stability in metaphyseal fragments of osteoporotic bone and a plate traction screw to compress the fracture. While this application addresses the poor holding power of the osteoporotic bone in metaphyseal fragments through the use of a screw with threads on the head to provide axial and angular stability, it does not address or provide a solution for the poor holding power of the osteoporotic bone for the traction screw passing through the plate. The obvious disadvantage of the described application is that such a fixation does not address the risk of loss of holding of the plate traction screw on account of the osteoporotic nature of the bone. Such a loss of holding would result in a direct loss of stability of the fixation of the fracture that has been carried out which would lead to a poor clinical outcome.

Therefore the prior art search reveals an urgent and acute need for an improved system of bone plates and bone screws wherein bone screws that are used to compress the fracture through a hole in the plate must also be locked in a relationship of angular and axial stability in the same plate hole. Further there clearly exists a need for bone screws that are enabled to be used as compression as well as locking screws that can compress the fracture in cooperation with a suitably designed bone plate and also be locked in a fixed angular relationship with the bone plate thereby ensuring angular and axial stability, without the use of any additional connection or mechanism that would cause a cumbersome additional step and further add an additional interface that could result in weakening of the bone screw-bone plate assembly.

OBJECTS OF THE INVENTION

One object of the invention is to provide a bone plate with a combination hole, which can receive a bone screw that can compress bone fragments and also be securely locked in a relationship of angular and axial stability with the bone plate, without the use of any other additional element that may add another cumbersome operative step.

Another object of the invention is to provide a combination bone screw that can be used through the combination hole of the bone plate of the instant invention, enabling compression of the fractured fragments of the bone and subsequently locking into the bone plate in a relationship of angular and axial stability with the bone plate of the instant invention.

Another object of the invention is to provide a bone plate with a combination hole that enables the use of a bone screw that can be used as a compression screw, a locking screw or any combinations thereof.

Another objective of the invention is to provide a process of stabilizing fractured fragments of bone comprising a bone plate with a combination hole, combination bone screw, compression bone screw, locking bone screw and any combinations thereof.

SUMMARY OF THE INVENTION

The instant invention discloses a bone plate system wherein the bone plate comprises a plurality of holes, at least one hole being a combination hole that can receive a combination screw that can compress fracture fragments and lock the screw in the bone plate resulting in compression as well as axial and angular stabilization of the fractured fragments of the bone, a combination screw that can be inserted in the combination hole of the bone plate of the instant invention that can cause fracture compression to occur in cooperation with the combination hole of the bone plate and be locked into the hole in the bone plate in a secure relationship of axial and angular stability. The invention further discloses, a bone plate system comprising of a bone plate with a plurality of holes, at least one hole being a combination hole and other holes enabled to receive combination screws, compression screws, locking screws, intraoperative temporary stabilization devices and combinations thereof. Further the invention relates to a process of stabilizing fractured fragments of bone comprising a bone plate with a combination hole, combination bone screw, compression bone screw, locking bone screw, intraoperative temporary stabilization devices and any combinations thereof.

DETAILED DESCRIPTION OF THE INVENTION

The instant invention relates to bone plates and bone plate assemblies used for compression and stabilization of fragments of a fractured bone.

Typically the human skeletal system is made up of bones that have a head and a shaft portion. It is well understood that fractures to bones are approached differently, dependent on various factors, some of which are the position and orientation of the fracture, the number of fragments, the extent of damage to surrounding soft tissues and the age and condition of the bone such as osteoporosis. Treatment of fractures generally comprise of systems or assemblies of bone plates with holes in them to receive bone screws. The process of treatment typically includes a step of compressing fractured fragments of the bone towards each other using the bone plate and screw assembly. Recent inventions in this field include bone plates wherein holes that have not been used for compressing fractured fragments may receive screws with threaded heads, which do not compress the bone fragments, but lock the bone plate with the screw, to achieve axial and angular stability of such screws.

The bone plate of the invention comprises an upper surface, a lower surface, the lower surface being the bone contacting surface and a plurality of holes, arranged along the longitudinal axis of the bone plate to receive bone screws. At least one hole of the bone plate, extending from the upper surface to the lower surface of the bone plate, herein referred to as a combination hole, comprises of a first section extending from the lower bone contacting surface of the plate, having a slot oriented along the longitudinal axis of the plate, with the length of the slot, SL, not exceeding 12 mm and the width of the slot, SW, not exceeding 6 mm, extending to a partial thickness of the plate, with the height of the slot in a ratio with the thickness of the plate in the range of 0.25:1 to 0.75:1, a second section that has a ramp that enables the gliding of a bone screw, with an included angle, θ, ranging from 5 deg. to 75 deg., a third section that comprises of a conical bored hole extending from the second section, with a smaller diameter, D1, not less than 3 mm, to the upper surface of the plate, with a larger diameter, D2, not less than 4 mm, and having circumferential, multi-start, conical threads in the bored hole extending along the complete periphery of the bored hole, wherein the smaller diameter of the bored hole, D1, is greater than the length of the slot along the longitudinal axis, with the surface of the smaller diameter D1 forming a bearing surface that is circumferential to the upper edge of the ramp. The bone plate may optionally include holes other than the combination hole that may be configured to receive conventional bone screws with spherical heads to compress fracture fragments, bone screws with threaded heads (locking bone screws) to lock with the bone plate in an axially stable manner, other openings of different sizes and configurations to stabilize fractured fragments in a temporary or permanent manner and various combinations thereof.

The instant invention further comprises of a plurality of bone screws, herein referred to as a combination bone screw, a compression bone screw and a locking bone screw.

The combination bone screw comprises of a head with a conical, multi-start, threaded section that threadably engages with the corresponding conical threaded section of the combination hole in the plate, a lower surface at the end of the threaded section that may optionally rest on the corresponding bearing surface of the combination hole in the bone plate of the instant invention, a second section with a spherical undersurface adjacent to the threaded section, which glides over the ramp in the combination hole of the plate and a shaft section with bone engaging threads. The bone engaging threads may optionally have a profile of a 'V' thread or a buttress thread or any other suitable thread form, with a thread angle varying from about 45 degrees to about 60 degrees. The head of the combination bone screw further comprises of a suitable internal slot that is used to insert and tighten the screw into the bone plate or the bone. The tip of the screw may optionally further include self-drilling and/or self tapping features.

The compression bone screw comprises of a head with a spherical undersurface which glides over the ramp in the combination hole of the plate, the head having a diameter lower than the smaller diameter of the conical threaded hole in the combination hole of the plate of the instant invention, and a shaft section with bone engaging threads. The bone engaging threads may optionally have a profile of a 'V' thread or a buttress thread or any other suitable thread form with a thread angle varying from about 45 degrees to about 60 degrees. The compression bone screw further possesses a suitable internal slot that is used to insert and tighten the screw into the bone plate or the bone. The tip of the screw may optionally further include self-drilling and/or self tapping features.

The locking bone screw comprises of a head with a conical, multi-start, threaded section that threadably engages with corresponding threads of holes in the bone plate of the instant invention, that are configured to receive only locking bone screws and a shaft section with bone engaging threads. The bone engaging threads may optionally have a profile of a 'V' thread or a buttress thread or any other suitable thread form with a thread angle varying from about 45 degrees to about 60 degrees. The locking bone screw further possesses a suitable internal slot that is used to insert and tighten the screw into the bone plate or the bone. The tip of the screw may optionally further include self-drilling and/or self tapping features.

The invention further comprises a drill guide comprising of a central section, a neutral guide attached to the central section with a central hole and having a tip opposite to the part attached to the central section, configured to threadably engage with the combination hole of the invention and further a load guide attached to the central section with an eccentric hole and having a tip opposite to the part attached to the central section, configured to threadably engage with the combination hole of the invention. The drill guide drills holes in the fractured fragments of bone with the guide coupled to at least one hole of the bone plate to determine position of bone screws.

In accordance with the instant invention, the preferred process for fracture fixation of fragments of a fractured bone comprises of drilling holes in fractured fragments of bone with a drill guide coupled to at least one hole of the bone plate to determine position of bone screws; securing one of the fragments of the fractured bone to the bone plate using at least one bone screw placed in a neutral position, wherein, the placement of the combination bone screw is such that the screw does not cause fracture compression to occur but only gets locked in an angularly stable position, and, the placement of a combination bone screw in the opposing fracture fragment, using at least one combination bone screw, placed in a load position, wherein, the placement of the combination bone screw is such that the screw whilst insertion, causes fracture compression to occur and subsequent to compression, gets locked in an angularly stable position, with a further plurality of bone screws inserted to secure the remainder of the plate holes in the bone plate.

Bone plates and bone screws of the instant invention are made of biocompatible materials selected from a group comprising of stainless steel and its various grades and alloys, titanium and its various grades and alloys, chromium-cobalt alloy and its various grades, various grades of biocompatible polymers such as ultra high molecular weight polyethylene, poly-L-lactide and other such biodegradable polymers, and such like, that are proven to be biocompatible and safe to be used in subjects such as humans and animals in need of treatment of bone fractures using the bone plates and screws.

According to one of the preferred embodiments of this invention, a bone plate comprises of an upper surface, a lower surface, the lower surface being the bone contacting surface, and a plurality of holes, with at least one combination hole extending from the upper surface to the lower surface of the bone plate, that optionally receives a combination bone screw that compresses the fracture and locks in the hole, a locking bone screw that locks in the hole, or a compression bone screw that compresses the fracture.

In another exemplary embodiment, the bone plate of the instant invention, comprises of an upper surface, a lower surface, said lower surface being the bone contacting surface, and a plurality of holes, with at least one or more combination holes of the bone plate, extending from the upper surface to the lower surface of the bone plate, that may optionally receive a combination bone screw that compresses the fracture and locks in the hole, a locking bone screw that locks in the hole, or a compression bone screw that compresses the fracture, and, at least one or more holes, extending from the upper surface to the lower surface of that bone plate, that are configured to receive either only conventional bone screws, or only locking bone screws or combinations thereof.

In another exemplary embodiment, the bone plate of the instant invention, comprises of an upper surface, a lower surface, the lower surface being the bone contacting surface, and a plurality of holes, with at least one or more combination holes of the bone plate, extending from the upper surface to the lower surface of the bone plate, configured to receive a combination bone screw that compresses the fracture and locks in the hole, a locking bone screw that locks in the hole, or a compression bone screw that compresses the fracture, and further, at least one or more holes, extending from the upper surface to the lower surface of the bone plate, that are configured to receive only locking bone screws.

In yet another embodiment, the bone plate of the instant invention, comprises of an upper surface, a lower surface, the lower surface being the bone contacting surface, and a plurality of holes, with at least one or more combination holes of the bone plate, extending from the upper surface to the lower surface of the bone plate, configured to receive a combination bone screw that compresses the fracture and locks in the hole, a locking bone screw that locks in the hole, or a compression bone screw that compresses the fracture, further, at least one or more holes, extending from the upper surface to the lower surface of the bone plate, that are configured to receive only locking bone screws, and further, at least one or more slots, extending from the upper surface to the lower surface of the bone plate, that are configured to receive a bone screw that may be used for elevation of one or more of the bone fragments.

Any of the above mentioned embodiments of the bone plate of the instant invention optionally includes at least one or more openings that receives temporary fixation devices for intraoperative temporary stabilization of one or more fractured fragments.

Any of the above mentioned embodiments of the bone plate of the instant invention, may further, be configured with a suitable cross section, such as a trapezoidal cross section, to reduce the extent of contact surface of the bone plate with the underlying bone.

In accordance to the various embodiments of the invention, it is apparent to one skilled in the art that considerations of bone sizes depending on subjects in need of treatment of fractured fragments of the bone will determine the dimensional variations in the bone plate with respect to thickness, length, width, profile and shape, intra as well as inter. Like wise varying dimensions of the combination hole, varying diameters of the combination screws, compression screws and locking screws, both head as well as bone engaging portions, varying major and minor diameters, pitch, lead, profile and thread form of the threads of the combination hole, threads of the head of the combination screw and bone engaging threads of the combination screw, compression screw, and, locking screw, and, varying angles formed by the axis of the combination hole with the longitudinal plate axis are deemed to be covered by the invention.

DETAILED DESCRIPTION OF THE DRAWINGS

Figure 1A:
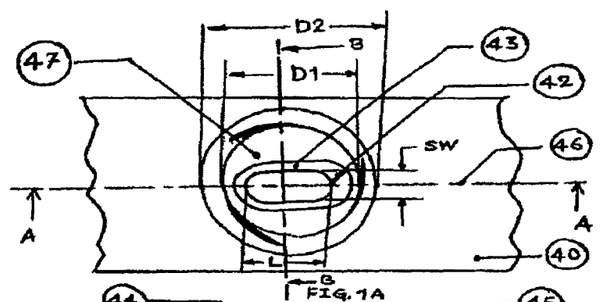
FIG. 1A: A top view of the combination hole in an exemplary bone plate
Figure 1B:
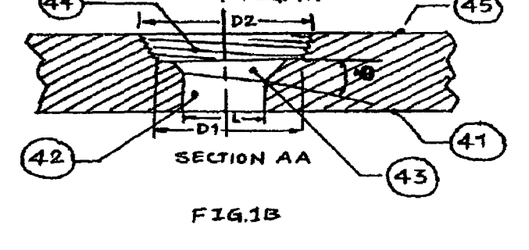
FIG. 1B: A cross section along section A-A of FIG. 1A illustrating the combination hole

FIGS. 1A, 1B, 6A and 6B show different views of a portion of the bone plate according to a preferred embodiment of the instant invention. The bone plate of the instant invention comprises of a plurality of holes with different configurations. However, for the purpose of ease of illustration and to describe an exemplary embodiment of the instant invention, only a portion of the bone plate 40 is shown in FIGS. 1A and 1B.

The bone plate 40 shown in FIGS. 1A, 1B, 6A and 6B comprises of a lower bone contacting surface 41, a slot 42, oriented along the longitudinal axis 46, a ramp 43 that enables gliding of a bone screw, a conical, threaded bored hole 44, with a smaller diameter D1 and a larger diameter D2, a bearing surface 47 and an upper surface 45.

Figure 2:
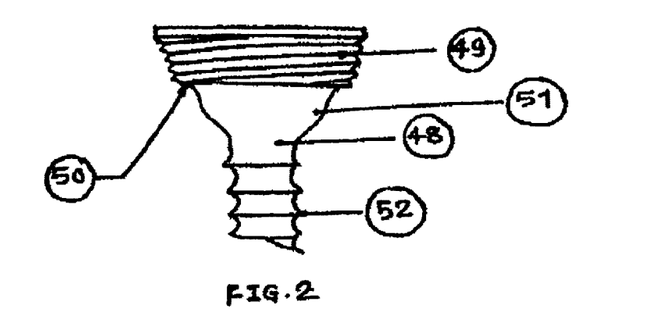
FIG. 2: Elevation of combination bone screw

The combination bone screw 48 shown in FIG. 2 comprises of a head with a conical, multi-start threaded section 49 that threadably engages with the corresponding conical threaded section of the combination hole in the plate, a bearing surface 50 that may optionally rest on the corresponding bearing surface 47 of the combination hole in the plate of the instant invention, a spherical undersurface 51 which glides over the ramp in the combination hole of the plate and a shaft with bone engaging threads 52. The combination bone screw 48 may have a major diameter of the bone engaging threads 52 ranging from 1.0 mm to 10.0 mm. In certain embodiments, it is desirable for the combination bone screw to have a uniform lead of the head threads 49 and the bone engaging threads 52, wherein, the thread pitch of the head threads 49 is such that the lead of these threads is the same as the lead of the bone engaging threads 52.

Figure 3:
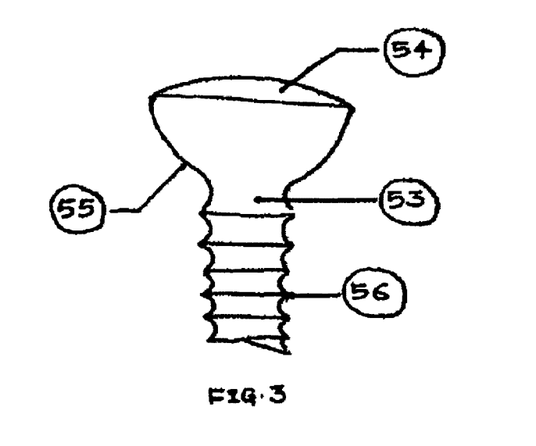
FIG. 3: Elevation of compression bone screw

The compression bone screw 53 shown in FIG. 3, comprises of a head 54 with a spherical undersurface 55 which glides over the ramp in the combination hole of the plate and a shaft with bone engaging threads 56. The compression bone screw 53 may have a major diameter of the bone engaging threads 56 ranging from 1.0 mm to 10.0 mm.

Figure 4:
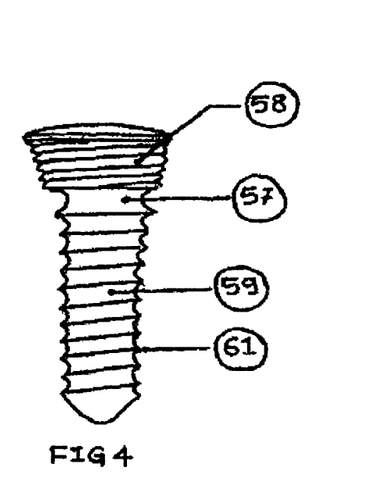
FIG. 4: Elevation of locking bone screw
Figure 5:
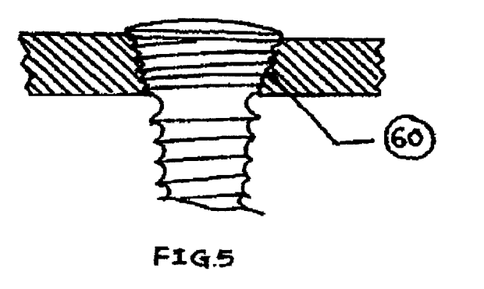
FIG. 5: Assembly of locking bone screw with locking hole of the bone plate
Figure 6A:
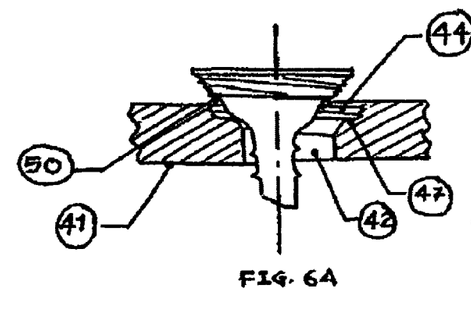
FIG. 6a: A cross section along section A-A of FIG. 1A illustrating the combination hole and additionally representing the combination screw in the combination hole
Figure 6B:
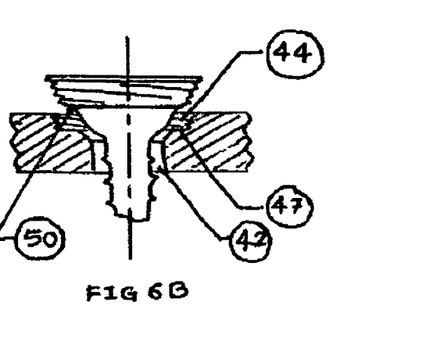
FIG. 6b: A cross section along section B-B of FIG. 1A illustrating the combination hole and additionally representing the combination screw in the combination hole

The locking bone screw 57 shown in FIG. 4 and FIG. 5 comprises of a head with a conical, multi-start threaded section 58 that threadably engages with corresponding threads of holes 60 in the bone plate of the instant invention that are configured to receive only locking bone screws 57, and a shaft section 59 with bone engaging threads 61. In certain embodiments, it is desirable for the locking bone screw to have a uniform lead of the head threads 58 and the bone engaging threads 61, wherein, the thread pitch of the head threads 58 is such that the lead of these threads is the same as the lead of the bone engaging threads 61. The locking bone screw 57 may have a major diameter of the bone engaging threads 61 ranging from 1.0 mm to 10.0 mm.

Figure 7:
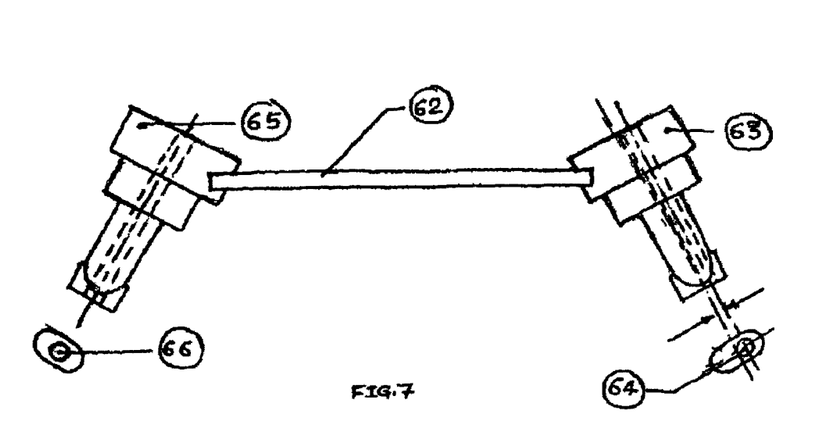
FIG. 7: Schematic representation of a double headed drill guide which enables placement of the combination bone screw in the combination hole of the plate in either neutral (no compression of fracture fragments) or load (compression of fractured fragments) positions

The double headed drill guide 62 shown in FIG. 7, comprises of a load drill guide 63, which is eccentrically placed through hole 64, that enables the placement of a drill hole in the bone through the combination hole of the plate in a position that allows compression of the fracture fragments to be caused on the insertion of a combination bone screw through the combination hole of the plate into the drilled hole in the bone, and, a neutral drill guide 65, with a centrally placed through hole 66, that enables the placement of a drill hole in the bone through the combination hole of the plate in a position that does not cause compression of the fracture fragments on the insertion of a combination bone screw through the combination hole of the plate into the drilled hole in the bone.

Many changes, modifications, variations and applications of the subject invention will become apparent to those skilled in the art after consideration of the specification. All such changes, modifications, alterations and other uses and applications which do not depart from the spirit and scope of the invention are deemed to be covered by the invention.

We claim:

1. A bone plate assembly comprising a bone plate and bone screws wherein:
   (a) said bone plate comprises, an upper surface, a bone contacting lower surface, and a plurality of holes to receive bone screws, at least one said hole being a combination hole, and
   (b) said bone screws comprise at least one combination bone screw for the compression and stabilization of fragments of a fractured bone,
   wherein said combination hole comprises:
      a first depth section extending from the bone contacting lower surface of said plate, having an elongated slot oriented along a longitudinal axis of said plate, extending from the bone contacting lower surface of the plate through a partial thickness of said plate,
      a second intermediate depth section that comprises a ramp, and a third depth section that comprises a conical bored hole extending from the second intermediate depth section to a circular periphery of the upper surface of the plate, the conical bored hole having a smaller diameter, D1, and a larger diameter, D2, and comprising circumferential, multi-start, conical threads in the bored hole extending entirely around the circular periphery of the bored hole, wherein the smaller diameter of the bored hole, D1, is greater than or equal to the length of the slot along the longitudinal axis, with a surface of the smaller diameter D1 forming a bearing surface that is circumferential to an upper edge of the ramp.

2. The bone plate assembly as claimed in claim 1 wherein said bone plate comprises a plurality of holes arranged along the longitudinal axis of the bone plate to receive bone screws, with at least one said hole being a combination hole extending from said upper surface to said bone contacting lower surface of said bone plate.

3. The bone plate assembly as claimed in claim 1 wherein said plurality of holes are configured to receive screws selected from the group comprising said combination bone screw, locking bone screws, compression bone screws, temporary fixation devices and combinations thereof.

4. The bone plate assembly as claimed in claim 1 wherein said plate is configured with a cross section to reduce the contact surface of said plate with the bone.

5. The bone plate assembly as claimed in claim 1 wherein said combination bone screw comprises a shaft section with bone engaging threads, adjacent to a spherical section configured to glide over the ramp in said combination hole of said bone plate, a head with a conical, multi-start, threaded section that threadably engages with the corresponding threaded section of said combination hole in said plate, and a lower surface at the end of the threaded section that rests on the corresponding bearing surface of said combination hole in said bone plate.

6. The bone plate assembly as claimed in claim 5, wherein said head of said combination bone screw comprises an internal slot to insert and tighten the screw into the bone plate or the bone.

7. The bone plate assembly as claimed in claim 5, wherein said tip of said combination bone screw comprises self-drilling features, self tapping features, or both self-drilling and self tapping features.

8. The bone plate assembly comprising a bone plate and bone screws as claimed in claim 1 wherein said assembly is made of biocompatible materials.

9. The bone plate assembly as claimed in claim 1 wherein said assembly comprises a drill guide having:
 a central section,
 a neutral guide attached to the central section with a central hole and having a tip, said tip of said neutral guide being configured to threadably engage with said combination hole; and
 a load guide attached to the central section with an eccentric hole and having a tip, configured to threadably engage with said combination hole.

10. The bone plate assembly as claimed in claim 9 wherein said assembly comprises two drill guides, including:
 a neutral guide with a central hole having a tip configured to threadably engage with said combination hole; and
 a load guide with an eccentric hole having a tip configured to threadably engage with said combination hole.

11. The bone plate assembly as claimed in claim 9, wherein:
 said at least one drill guide is a neutral guide with a central hole having a tip of said neutral guide being configured to threadably engage with said combination hole; and
 said neutral guide is releasably coupled to at least one combination hole of said bone plate to determine the position of a drill hole for said at least one combination bone screw;
 wherein said neutral guide positions said drill hole so that said at least one combination bone screw does not cause compression of said fragments of said fractured bone.

12. The bone plate assembly as claimed in claim 9, wherein:
 said at least one drill guide is a load guide with an eccentric hole having a tip of said load guide being configured to threadably engage with said combination hole; and
 said load guide is releasably coupled to at least one combination hole of said bone plate to determine the position of a drill hole for said at least one combination bone screw;
 wherein said load guide positions said drill hole so that said at least one combination bone screw does cause compression of said fragments of said fractured bone.

13. The bone plate assembly as claimed in claim 9, wherein:
 said plurality of holes comprises at least two said combination bone screws and at least two said combination holes, including a first combination hole and a second combination hole; and
 said at least one drill guide comprises:
  (a) a load guide with an eccentric hole having a tip of said load guide being configured to threadably engage with said combination hole; and
  (b) a neutral guide with a central hole having a tip of said neutral guide being configured to threadably engage with said combination hole;
 wherein said neutral guide is releasably coupled to said first combination hole of said bone plate to determine the position of a first drill hole for a first of said two combination bone screws, so that said neutral guide positions said first drill hole so that insertion of said first combination bone screw fixes the said fracture fragment in a position of angular stability; and
 wherein said load guide is releasably coupled to said second combination hole of said bone plate to determine the position of a second drill hole for a second of said two combination bone screws, in the opposing fracture fragment, so that said load guide positions said second drill hole so that insertion of said second combination bone screw causes compression of said fragments of said fractured bone; and
 further insertion of said second combination bone screw causes said second combination bone screw to be locked to said bone plate in a position of angular stability.

14. A method for compression and stabilization of fragments of a fractured bone using the bone plate assembly as claimed in claim 9, comprising:
 a. drilling holes in said fractured fragments of bone with said drill guide, wherein said drill guide is coupled to at least one hole of said bone plate to determine a desired position of at least one bone screw;
 b. securing one of the fragments of the fracture to said bone plate by inserting at least one bone screw through one of the holes of said plate;
 c. inserting said combination bone screw through said combination hole in said bone plate into an opposing fracture fragment to cause fracture compression;

d. inserting said combination bone screw further through said combination hole for locking of said combination screw in a position angularly stable with said bone plate; and e. securing said bone plate to the various fragments of fractured bone with bone screws.

15. A method for compression and stabilization of fragments of a fractured bone using the bone plate assembly as claimed in claim 10, comprising:

a. drilling holes in said fractured fragments of bone with said drill guide, wherein said drill guide is coupled to at least one hole of said bone plate to determine a desired position of at least one bone screw;
   b. securing one of the fragments of the fracture to said bone plate by inserting at least one bone screw through one of the holes of said plate;
   c. inserting said combination bone screw through said combination hole in said bone plate into an opposing fracture fragment to cause fracture compression;
   d. inserting said combination bone screw further through said combination hole for locking of said combination screw in a position angularly stable with said bone plate; and
   e. securing said bone plate to the various fragments of fractured bone with bone screws.

16. A method for compression and stabilization of fragments of a fractured bone using the bone plate assembly as claimed in claim 11, comprising:

a. drilling holes in said fractured fragments of bone with said drill guide, wherein said drill guide is coupled to at least one hole of said bone plate to determine a desired position of at least one bone screw;
   b. securing one of the fragments of the fracture to said bone plate by inserting at least one bone screw through one of the holes of said plate;
   c. inserting said combination bone screw through said combination hole in said bone plate into an opposing fracture fragment to cause fracture compression;
   d. inserting said combination bone screw further through said combination hole for locking of said combination screw in a position angularly stable with said bone plate; and
   e. securing said bone plate to the various fragments of fractured bone with bone screws.

17. A method for compression and stabilization of fragments of a fractured bone using the bone plate assembly as claimed in claim 12, comprising:

a. drilling holes in said fractured fragments of bone with said drill guide, wherein said drill guide is coupled to at least one hole of said bone plate to determine a desired position of at least one bone screw;
   b. securing one of the fragments of the fracture to said bone plate by inserting at least one bone screw through one of the holes of said plate;
   c. inserting said combination bone screw through said combination hole in said bone plate into an opposing fracture fragment to cause fracture compression;
   d. inserting said combination bone screw further through said combination hole for locking of said combination screw in a position angularly stable with said bone plate; and
   e. securing said bone plate to the various fragments of fractured bone with bone screws.

18. A method for compression and stabilization of fragments of a fractured bone using the bone plate assembly as claimed in claim 13, comprising:

a. drilling holes in said fractured fragments of bone with said drill guide, wherein said drill guide is coupled to at least one hole of said bone plate to determine a desired position of at least one bone screw;
   b. securing one of the fragments of the fracture to said bone plate by inserting at least one bone screw through one of the holes of said plate;
   c. inserting said combination bone screw through said combination hole in said bone plate into an opposing fracture fragment to cause fracture compression;
   d. inserting said combination bone screw further through said combination hole for locking of said combination screw in a position angularly stable with said bone plate; and
   e. securing said bone plate to the various fragments of fractured bone with bone screws.

19. A method for compression and stabilization of fragments of a fractured bone using the bone plate assembly as claimed in claim 1, wherein:

bone plate assembly comprising two said combination bone screws and said plurality of holes comprises two said combination holes, including a first combination hole and a second combination hole; and
   at least one drill guide comprising:
   (a) a neutral guide with a central hole having a tip of said neutral guide being configured to threadably engage with said first combination hole;
   (b) a load guide with an eccentric hole having a tip of said load guide being configured to threadably engage with said second combination hole; and said method comprising:
   releasably coupling said neutral guide to said first combination hole of said bone plate and drilling a first drill hole in one of said fragments of fractured bone;
   positioning a first of said two combination bone screws in said first drill hole;
   releasably coupling said load guide to said second combination hole of said bone plate and drilling a second drill hole in another of said fragments of fractured bone;
   positioning a second of said two combination bone screws in said second drill hole so that said second of said two combination bone screws enables compression of said fragments of said fractured bone; and
   locking said second combination bone screw in an angularly stable position relative to said bone plate.

20. The bone plate assembly as claimed in claim 1 wherein said bone screw has a head section configured to achieve an axial travel along the longitudinal axis of the bone plate in order to compress two fractured fragments of bone and further configured to threadably engage in the combination hole after said axial travel to achieve a condition of angular stability with reference to said bone plate.

* * * * *